United States Patent
Hunt et al.

(10) Patent No.: US 10,494,349 B2
(45) Date of Patent: Dec. 3, 2019

(54) METHODS OF PREPARING REGIOSELECTIVE N-ALKYL TRIAZOLES

(71) Applicant: Corcept Therapeutics, Inc., Menlo Park, CA (US)

(72) Inventors: Hazel Hunt, Storrington (GB); Arjen Christiaan Breman, Weert (NL); Bas Wilhelmus Theodorus Gruijters, Gemert (NL)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 16/390,169

(22) Filed: Apr. 22, 2019

(65) Prior Publication Data
US 2019/0322629 A1 Oct. 24, 2019

Related U.S. Application Data

(60) Provisional application No. 62/661,446, filed on Apr. 23, 2018, provisional application No. 62/746,904, filed on Oct. 17, 2018.

(51) Int. Cl.
*C07D 249/06* (2006.01)
(52) U.S. Cl.
CPC .................... *C07D 249/06* (2013.01)

(58) Field of Classification Search
CPC ..................................................... C07D 249/06
See application file for complete search history.

(56) References Cited

FOREIGN PATENT DOCUMENTS

| CN | 102408385 A | 4/2012 |
|---|---|---|
| WO | 2013127028 A1 | 9/2013 |
| WO | 2015077530 A1 | 5/2015 |

OTHER PUBLICATIONS

Wang et al., Organic Letters, 2010, vol. 12, No. 20, 4632-4635.*
PCT/US2019/028473, "International Search Report and Written Opinion", dated Sep. 18, 2019, 9 pages.
Zhang et al., "Regioselective Synthesis of Polysubstituted N2-Alkyl/Aryl-1,2,3-Triazoles via 4-Bromo-5-iodo-1,2,3-triazole", Synlett, vol. 23, No. 7, 2012, pp. 1052-1056.

* cited by examiner

*Primary Examiner* — Sun Jae Yoo
(74) *Attorney, Agent, or Firm* — Kilpatrick Townsend & Stockton LLP (57) ABSTRACT

Methods of preparing N-2 alkylated triazoles substantially free from N-1 and N-3 alkylated triazoles are disclosed. The methods include one-step alkylation methods and two-step alkylation methods for the preparation of N-alkylated triazoles.

23 Claims, 1 Drawing Sheet

METHODS OF PREPARING REGIOSELECTIVE N-ALKYL TRIAZOLES

CROSS-REFERENCES TO RELATED APPLICATIONS

This application claims the benefit of, and priority to, U.S. Provisional Patent Application 62/661,446 filed Apr. 23, 2018 and U.S. Provisional Patent Application 62/746,904 filed Oct. 17, 2018, the contents of both of which applications are hereby incorporated by reference in their entireties.

BACKGROUND

The triazole is a heterocyclic organic five-membered ring with three nitrogen and two carbon atoms that is prevalent in biologically active compounds (Dheer, D. et al., *Bioorganic Chemistry* 2017, 71, 30-54; Haider, S. et al., *Inflammation & Cell Signalling* 2014, 1, 1-10 (http://dx.doi.org/10.14800/ics.95)). The triazole acts as an effective amide surrogate due to its strong dipole moment and possesses additional important features such as hydrogen bonding, dipole-dipole and pi-stacking interactions, and improved solubility (Dheer, D.). The N-1/N-3-substituted 1,2,3-triazole has been well-exploited, primarily due to advances in the azide-dipolarophile cycloaddition methodologies (i.e., Sharpless' Click variation of the Huisgen reaction (Wang, X-j. et al. *Organic Letters* 2010, 12, 4632-4635)). The N-2 substituted 1,2,3-triazole has been less well studied, since there are no effective general synthetic methods beyond several unselective or specialized syntheses. Thus the need exists for the regioselective preparation of N-2 substituted 1,2,3-triazoles (Wang, X-j.).

BRIEF SUMMARY

In one embodiment, the present invention provides a method of making a compound of Formula I:

(I)

substantially free of the compounds of Formula Ia and Formula Ib:

(Ia)

(Ib)

The method of making the compound of Formula I includes forming a first reaction mixture comprising a compound of Formula II:

(II)

a non-nucleophilic base, a first solvent, and a compound of Formula IIIa:

$$R^{1a}\text{-}LG^{1a} \quad \text{(IIIa)},$$

wherein the molar ratio of the compound of Formula IIIa to the compound of Formula II is greater than 1, under conditions suitable to form an intermediate mixture comprising the compound of Formula I and at least one compound of Formula Ia and Ib. The method also includes forming a second reaction mixture comprising the intermediate mixture, and a compound of Formula IIIb:

$$R^{1b}\text{-}LG^{1b} \quad \text{(IIIb)},$$

wherein the molar ratio of the compound of Formula IIIb to the compounds of the intermediate mixture is greater than 1, and wherein the second reaction mixture is mixed under conditions suitable to form at least one compound of Formula IVa or Formula IVb:

(IVa)

(IVb)

The method also includes forming a partition mixture comprising the second reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, IIIa, IIIb, IVa and IVb, $R^{1a}$ and $R^{1b}$ are independently methyl, ethyl, n-propyl, iso-propyl, n-butyl, sec-butyl, iso-butyl or cyclopropylmethyl; $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy; $LG^{1a}$ and $LG^{1b}$ are each independently Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, the present invention provides a method of making a compound of Formula I:

(I)

[Structure of Formula I: triazole with R² and R¹ᵃ substituents]

substantially free of the compounds of Formula Ia and Formula Ib:

(Ia)

[Structure of Formula Ia]

(Ib)

[Structure of Formula Ib]

The method of the present invention includes forming a first reaction mixture comprising a compound of Formula II:

(II)

[Structure of Formula II: triazole with R² and N-H]

a non-nucleophilic base, a first solvent, and a compound of Formula IIIa:

$$R^{1a}\text{-}LG^{1a} \quad \text{(IIIa)},$$

wherein the molar ratio of the compound of Formula IIIa to the compound of Formula II is greater than 1, and wherein the reaction mixture is mixed for at least two hours at or above room temperature under conditions suitable to form an intermediate mixture comprising the compound of Formula I and at least one compound of Formula Ia and Ib. The method also includes forming a second reaction mixture comprising the intermediate mixture, and a compound of Formula IIIb:

$$R^{1b}\text{-}LG^{1b} \quad \text{(IIIb)},$$

wherein the molar ratio of the compound of Formula III to the compounds of the intermediate mixture is greater than 1, and wherein the second reaction mixture is mixed for at least two hours at or above room temperature under conditions suitable to form at least one compound of Formula IVa or Formula IVb:

(IVa)

[Structure of Formula IVa]

(IVb)

[Structure of Formula IVb]

The method also includes forming a partition mixture comprising the second reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, IIIa, IIIb, IVa and IVb, $R^{1a}$ is methyl, ethyl, n-propyl, iso-propyl, n-butyl, sec-butyl, iso-butyl or cyclopropylmethyl; $R^{1b}$ is methyl, ethyl, n-propyl, iso-propyl, n-butyl, sec-butyl, iso-butyl or cyclopropylmethyl, such that $R^{1b}$ is different than $R^{1a}$; $LG^{1a}$ and $LG^{1b}$ are each independently Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, the present invention provides a method of making a compound of Formula I:

(I)

[Structure of Formula I]

substantially free of the compounds of Formula Ia and Formula Ib:

(Ia)

[Structure of Formula Ia]

(Ib)

[Structure of Formula Ib]

The method of the present invention includes forming a first reaction mixture comprising a compound of Formula II:

(II)

[Structure of Formula II]

the non-nucleophilic base, the first solvent, a compound of Formula IIIa:

$$R^{1a}\text{-}LG^{1a} \quad \text{(IIIa)},$$

and a compound Formula IIIb:

$$R^{1b}\text{-}LG^{1b} \quad \text{(IIIb),}$$

wherein the molar ratio of the compounds of Formula IIIa and IIIb to the compound of Formula II is greater than 2, and wherein the reaction mixture is mixed for at least two hours at or above room temperature under conditions suitable to form the compound of Formula I and at least one compound of Formula IVa or Formula IVb:

(IVa)

(IVb)

The method also includes forming a partition mixture comprising the first reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, IIIa, IIIb, IVa and IVb, $R^{1a}$ and $R^{1b}$ are the same and are methyl, ethyl, n-propyl, iso-propyl, n-butyl, sec-butyl, iso-butyl or cyclopropylmethyl; $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy; $LG^{1b}$ is Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, the present invention provides a method of making a compound of Formula I:

(I)

substantially free of the compounds of Formula Ia and Formula Ib:

(Ia)

(Ib)

including the step of forming a first reaction mixture of a compound of Formula II:

(II)

a non-nucleophilic base, a first solvent, and a compound of Formula III:

$$R^1\text{-}LG \quad \text{(III),}$$

wherein the molar ratio of the compound of Formula III to the compound of Formula II is greater than 2, and wherein the reaction mixture is mixed for at least two hours at or above room temperature under conditions suitable to form the compound of Formula I and at least one compound of Formula IVa or Formula IVb:

(IVa)

(IVb)

The method of the present invention also includes the step of forming a partition mixture including the first reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, III, IVa and IVb, $R^1$ is methyl, ethyl, n-propyl, iso-propyl, n-butyl, sec-butyl, iso-butyl or cyclopropylmethyl, $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy, LG is I or $OSO_2R^3$, and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

DETAILED DESCRIPTION

I. General

Figure 1:
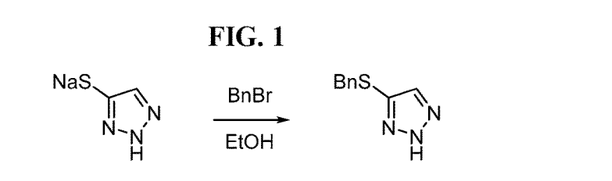
FIG. 1 shows the preparation of the compound of the Formula II having the structure 4-(benzylthio)-2H-1,2,3- triazole, via benzylation of the commercially available sodium 2H-1,2,3-triazole-4-thiolate.
Figure 2:
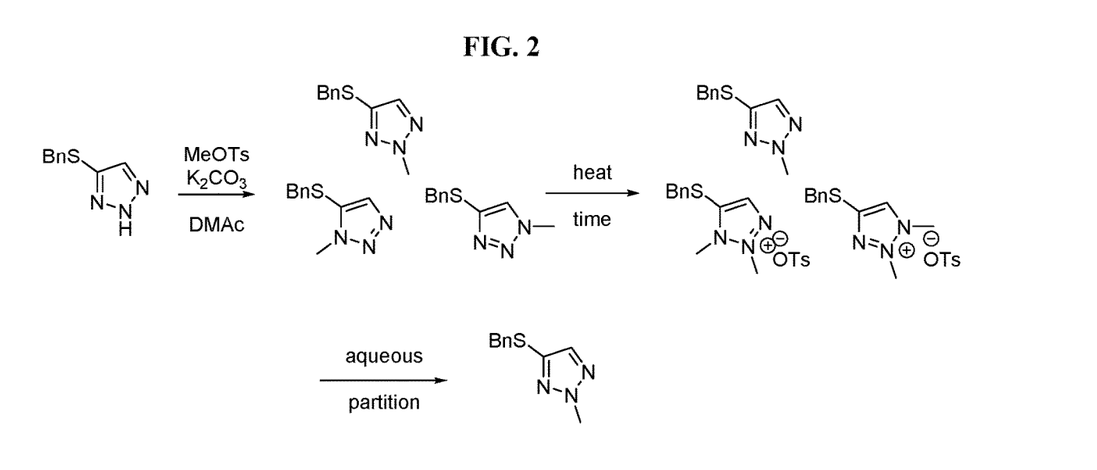
FIG. 2 shows the preparation of the compound of the Formula I having the structure 4-(benzylthio)-2-methyl-2H-1,2,3-triazole, via the N-alkylation of the compound of Formula II having the structure 4-(benzylthio)-2H-1,2,3-triazole.
Figure 3:
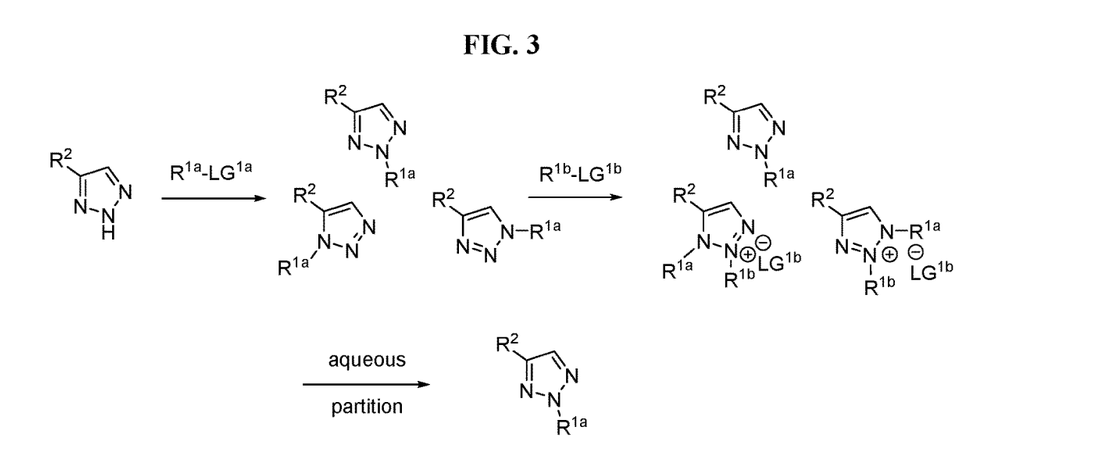
FIG. 3 shows the generic scheme for preparation of the compound of the Formula I via the two-step alkylation process.

The present invention provides a method of preparing N-2 alkylated triazoles such as 4-(benzylthio)-2-methyl-2H-1,2,3-triazole, substantially free from N-1 and N-3 alkylated triazoles. The key to the invention is the subsequent alkylation of any N-1 and N-3 alkylated triazoles that are formed, resulting in doubly-alkylated salts which are subsequently removed by an aqueous washing step.

II. Definitions

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Substantially free" refers to a composition of regioisomers, wherein the undesired regioisomer content is less than 5%, preferably less than 1%, more preferably less than 0.5% or even less than 0.1% by weight.

"Non-nucleophilic base" refers to a base that is a moderate to strong base but at the same time is a poor nucleophile. Representative non-nucleophilic bases include bases such as potassium carbonate, sodium carbonate, potassium tert-butoxide, and sodium tert-butoxide, as well as nitrogen bases, such as triethylamine, diisopropylethyl amine, N,N-diethylaniline, pyridine, 2,6-lutidine, 2,4,6-collidine, 4-dimethylaminopyridine, and quinuclidine.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, acetone, ethyl acetate, dimethylformamide, dimethylacetamide, acetonitrile and dimethyl sulfoxide. Representative non-polar solvents include alkanes (pentanes, hexanes, etc.), cycloalkanes (cyclopentane, cyclohexane, etc.), benzene, toluene, and 1,4-dioxane. Other solvents are useful in the present invention.

"Partition mixture" refers to an immiscible mixture of an organic solvent layer and an aqueous water layer used in solvent-solvent extractions in order to isolate a desired substance. Suitable organic solvents include, but are not limited to, hexane, diethyl ether, ethyl acetate, and dichloromethane. Suitable aqueous water layers include, but are not limited to, water, and various water soluble salt solutions, for example, 20% sodium chloride solution.

"Leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, iodide, mesylate, tosylate, triflate, 4-nitrobenzenesulfonate, 4-chlorobenzenesulfonate, sulfate, etc. One of skill in the art will recognize other leaving groups useful in the present invention.

"Alkyl" refers to a straight or branched acyclic hydrocarbon containing normal, secondary, or tertiary carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (s-Pn, s-Pentyl, —$CH(CH_3)CH_2CH_2CH_3$), 3-pentyl (—$CH(CH_2CH_3)_2$), 2-methyl-2-butyl (t-Pn, t-Pentyl, —$C(CH_3)_2CH_2CH_3$), 3-methyl-2-butyl (neo-Pn, neo-Pentyl, —$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Halogen" refers to F, Cl, Br, and I.

"Haloalkyl" refers to an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ haloalkyl). Examples of suitable haloalkyl groups include, but are not limited to, —$CF_3$, —$CHF_2$, —$CFH_2$, —$CH_2CF_3$, and the like.

"Alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —O-t-Bu), and the like.

"Haloalkoxy" refers to a group having the formula —O-haloalkyl, in which a haloalkyl group, as defined above, is attached to the parent molecule via an oxygen atom. The alkyl portion of a haloalkyl group can have 1 to 20 carbon atoms (i.e., $C_1$-$C_{20}$ haloalkoxy), 1 to 12 carbon atoms (i.e., $C_1$-$C_{12}$ haloalkoxy), or 1 to 6 carbon atoms (i.e., $C_1$-$C_6$ haloalkoxy). Examples of suitable haloalkoxy groups include, but are not limited to, —OCH$_2$F, —OCHF$_2$, and —OCF$_3$.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

"Room temperature" is the range of air temperatures generally considered to be suitable for human occupancy, or between about 15 degrees Celsius (59 degrees Fahrenheit) and 25 degrees Celsius (77 degrees Fahrenheit).

"Nitro" refers to —NO$_2$.

"Iodide" refers to —I.

"Benzyl" refers to —CH$_2$-Ph, where "Ph" refers to phenyl.

"Tosyl" (Ts) refers to the toluene-4-sulfonyl radical, —SO$_2$C$_6$H$_4$CH$_3$.

"Tosylate" (OTs) refers to the anion of p-toluenesulfonic acid, —OSO$_2$C$_6$H$_4$CH$_3$.

"Tautomer" refers to one of two or more structural isomers which exist in equilibrium and which are readily converted from one isomeric form to another. For example, the tautomerism of 1,2,3-triazole in aqueous solution has been described (Albert, A. et al., *J. Chem. Soc. Perkin Trans. II* 1989, 1903-05).

It will be apparent to one skilled in the art that certain compounds of this invention may exist in tautomeric forms, all such tautomeric forms of the compounds being within the scope of the invention. For example, compounds of the Formula II:

(II)

may exist in such tautomeric forms as compounds of the Formula IIa and Formula IIb:

(IIa)

(IIb)

All such tautomeric forms of the compounds being within the scope of the invention.

III. Method of Preparing Triazoles of Formula I

The compounds of Formula I can be prepared by a variety of means. For example, the compounds of Formula I can be prepared as described below, via N-alkylation of a compound of Formula II with a compound of Formula III, namely methyl p-toluenesulfonate, or methyl iodide.

In one embodiment, the present invention provides a method of making a compound of Formula I:

(I)

substantially free of the compounds of Formula Ia and Formula Ib:

(Ia)

(Ib)

The method of making the compound of Formula I includes forming a first reaction mixture comprising a compound of Formula II:

(II)

a non-nucleophilic base, a first solvent, and a compound of Formula IIIa:

R$^{1a}$-LG$^{1a}$ (IIIa), wherein the molar ratio of the compound of Formula IIIa to the compound of Formula II is greater than 1, under conditions suitable to form an intermediate mixture comprising the compound of Formula I and at least one compound of Formula Ia and Ib. The method also includes forming a second reaction mixture comprising the intermediate mixture, and a compound of Formula IIIb:

R$^{1b}$-LG$^{1b}$ (IIIb), wherein the molar ratio of the compound of Formula IIIb to the compounds of the intermediate mixture is greater than 1, and wherein the second reaction mixture is mixed under conditions suitable to form at least one compound of Formula IVa or Formula IVb:

The method also includes forming a partition mixture comprising the second reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, IIIa, IIIb, IVa and IVb, $R^{1a}$ and $R^{1b}$ are independently methyl, ethyl, n-propyl, iso-propyl, n-butyl, sec-butyl, iso-butyl or cyclopropylmethyl; $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy; $LG^{1a}$ and $LG^{1b}$ are each independently Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

Any suitable non-nucleophilic base can be used in the method of the present invention. Representative non-nucleophilic bases include, but are not limited to, potassium carbonate, sodium carbonate, cesium carbonate, potassium tert-butoxide, and sodium tert-butoxide. In some embodiments, the non-nucleophilic base can be potassium carbonate, sodium carbonate, potassium tert-butoxide, or sodium tert-butoxide. In some embodiments, the non-nucleophilic base can be potassium carbonate, or sodium carbonate. In some embodiments, the non-nucleophilic base can be potassium carbonate. In some embodiments, the non-nucleophilic base can be sodium tert-butoxide.

The first solvent can be any suitable solvent. Representative solvents include, but are not limited to, acetone, acetonitrile, dimethylacetamide, tetrahydrofuran, dimethylsulfoxide, toluene, methyl tert-butyl ether, ethanol, dimethylformamide, or combinations thereof. In some embodiments, the first solvent can be dimethylacetamide, methyl tert-butyl ether, ethanol, or combinations thereof. In some embodiments, the first solvent can be dimethylacetamide. In some embodiments, the first solvent can be dimethylformamide.

Any suitable combination of non-nucleophilic base and solvent can be used in the methods disclosed herein. In some embodiments, the non-nucleophilic base can be potassium carbonate, sodium carbonate, potassium tert-butoxide, or sodium tert-butoxide, and the solvent can be acetone, acetonitrile, dimethylacetamide, tetrahydrofuran, dimethylsulfoxide, toluene, methyl tert-butyl ether, ethanol, dimethylformamide, or combinations thereof. In some embodiments, the non-nucleophilic base can be potassium carbonate or sodium carbonate, and the solvent can be dimethylacetamide, methyl tert-butyl ether, ethanol, or combinations thereof. In some embodiments, the non-nucleophilic base can be potassium tert-butoxide or sodium tert-butoxide, and the solvent can be selected from dimethylacetamide, methyl tert-butyl ether, ethanol, or combinations thereof. In some embodiments, the non-nucleophilic base can be sodium tert-butoxide, and the solvent can be dimethylacetamide, methyl tert-butyl ether, ethanol, or combinations thereof. In some embodiments, the non-nucleophilic base can be potassium carbonate, and the solvent can be selected from dimethylacetamide, methyl tert-butyl ether, ethanol, or combinations thereof. In some embodiments, the non-nucleophilic base can be potassium carbonate, and the solvent can be dimethylacetamide.

The N-alkylation of the compound of Formula II can be performed in one step or two steps. When the N-alkylation is performed using two steps, the first N-alkylation step can include any suitable molar ratio of the compound of Formula IIIa to the compound of Formula II. Representative molar ratios include, but are not limited to, at least 1, or 2, 3, 4, 5, 6, 7, 8, 9 or greater than 10. The molar ratio of the compound of Formula IIIa to the compound of Formula II can be from 1 to 10, or from 2 to 5. In some embodiments, the molar ratio of the compound of Formula IIIa to the compound of Formula II can be at least 1. In some embodiments, the molar ratio of the compound of Formula IIIa to the compound of Formula II can be from 1 to 4. In some embodiments, the molar ratio of the compound of Formula IIIa to the compound of Formula II can be at least 1. In some embodiments, the molar ratio of the compound of Formula IIIa to the compound of Formula II can be greater than 1.

The second N-alkylation step can include any suitable molar ratio of the compound of Formula IIIb to the compounds of the intermediate mixture. Representative molar ratios include, but are not limited to, at least 1, or 2, 3, 4, 5, 6, 7, 8, 9 or greater than 10. The molar ratio of the compound of Formula IIIb to the compounds of the intermediate mixture can be from 1 to 10, or from 2 to 5. In some embodiments, the molar ratio of the compound of Formula IIIb to the compounds of the intermediate mixture can be at least 1. In some embodiments, the molar ratio of the compound of Formula IIIb to the compounds of the intermediate mixture can be from 1 to 4. In some embodiments, the molar ratio of the compound of Formula IIIb to the compounds of the intermediate mixture can be at least 2. In some embodiments, the molar ratio of the compound of Formula IIIb to the compounds of the intermediate mixture can be greater than 2.

When the N-alkylation is performed using a single step, the N-alkylation step can include any suitable molar ratio of the compounds of Formula IIIa and Formula IIIb to the compound of Formula II. Representative molar ratios include, but are not limited to, at least 2, or 3, 4, 5, 6, 7, 8, 9 or greater than 10. The molar ratio of the compounds of Formula IIIa and Formula IIIb to the compound of Formula II can be from 2 to 10, or from 2 to 5, or from 3 to 5. In some embodiments, the molar ratio of the compounds of Formula IIIa and Formula IIIb to the compound of Formula II can be at least 2. In some embodiments, the molar ratio of the compounds of Formula IIIa and Formula IIIb to the compound of Formula II can be from 2 to 4. In some embodiments, the molar ratio of the compound of Formula IIIa and Formula IIIb to the compounds of Formula II can be about 4.

The N-alkylation steps of forming the compound of Formula I can be performed for any suitable reaction time. For example, the reaction time can be for minutes, hours, or days. In some embodiments, the reaction time can be for several hours, such as at least eight hours. In some embodiments, the reaction time can be for several hours, such as at least overnight. In some embodiments, the reaction time can be for several days. In some embodiments, the reaction time can be for at least two hours. In some embodiments, the reaction time can be for at least eight hours. In some embodiments, the reaction time can be for at least several days. In some embodiments, the reaction time can be for about two hours, or for about 4 hours, or for about 6 hours, or for about 8 hours, or for about 10 hours, or for about 12 hours, or for about 14 hours, or for about 16 hours, or for about 18 hours, or for about 20 hours, or for about 22 hours, or for about 24 hours. In some embodiments, the reaction time can be for about 1 day, or for about two days, or for about three days, or for about four days, or for about five days, or for about six days, or for about a week, or for about more than a week.

The reaction mixture of the N-alkylation steps of forming the compound of Formula I can be performed at any suitable reaction temperature. Representative temperatures include, but are not limited to, below room temperature, at room temperature, or above room temperature. Other temperatures useful in the methods disclosed herein include from about −40° C. to about 65° C., or from about room temperature to about 40° C., or from about 40° C. to about 65° C., or from about 40° C. to about 60° C. The first reaction mixture can be at a temperature of about room temperature, or at a temperature of about 15° C., or at about 20° C., or at about 25° C. or at about 30° C., or at about 35° C., or at about 40° C., or at about 45° C., or at about 50° C., or at about 55° C., or at about 60° C., or at about 65° C. In some embodiments, the first reaction mixture can be at a temperature of room temperature or above room temperature. In some embodiments, the first reaction mixture can be a temperature of from about room temperature to about 40° C. In some embodiments, the first reaction mixture can be a temperature of from about 40° C. to about 60° C.

The method of preparing the compound of Formula I also includes forming a partition mixture of the first or second reaction mixture, water and an organic solvent to form an aqueous layer and an organic layer. In some embodiments, the organic solvent can be formed from diethyl ether, ethyl acetate, or dichloromethane. In some embodiments, the organic solvent can be dichloromethane. In some embodiments, the organic solvent can be ethyl acetate. In some embodiments, the partition mixture can be formed by combining the first reaction mixture, water, and dichloromethane. In some embodiments, the partition mixture can be formed by combining the first reaction mixture, water, and ethyl acetate.

$R^{1a}$ and $R^{1b}$ of Formula I, Ia, Ib, IIIa, IIIb, IVa, IVb are as defined above. In some embodiments, $R^{1a}$ and $R^{1b}$ can independently be methyl, ethyl, n-propyl, iso-propyl, n-butyl, sec-butyl, iso-butyl, or cyclopropylmethyl. In some embodiments, $R^{1a}$ and $R^{1b}$ can independently be methyl, ethyl, or cyclopropylmethyl. In some embodiments, $R^{1a}$ can be ethyl, n-propyl, iso-propyl, n-butyl, sec-butyl, iso-butyl or cyclopropylmethyl, and $R^{1b}$ can be methyl. In some embodiments, $R^{1a}$ can be iso-propyl, and $R^{1b}$ can be methyl. In some embodiments, $R^{1a}$ and $R^{1b}$ can be methyl.

$R^2$ of Formula I, Ia, Ib, II, IVa, IVb is as defined above. In some embodiments, $R^2$ can be halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy. In some embodiments, $R^2$ can be $SCH_2Ar$, wherein Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy. In some embodiments, $R^2$ can be $SCH_2Ar$, wherein Ar is phenyl optionally substituted with 1-3 $R^{2a}$ groups each independently halogen, $C_1$-$C_6$ alkyl, or $C_1$-$C_6$ haloalkyl. In some embodiments, $R^2$ can be $SCH_2Ar$, wherein Ar is phenyl or p-tolyl. In some embodiments, $R^2$ can be $SCH_2Ar$, where Ar is phenyl. In some embodiments, $R^2$ can be halogen.

In some embodiments, $LG^{1a}$ of Formula IIIa and $LG^{1b}$ of Formula IIIb can independently be any suitable leaving group. In some embodiments, $LG^{1a}$ and $LG^{1b}$ can independently be Br, I or $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $LG^{1a}$ and $LG^{1b}$ can independently be I or $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $LG^{1a}$ can be Br or I. In some embodiments, $LG^{1a}$ can be Br.

In some embodiments, $LG^{1b}$ can be $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $LG^{1b}$ can be $OSO_2R^3$, wherein $R^3$ is $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $LG^{1b}$ can be $OSO_2R^3$, wherein $R^3$ is $C_6$-$C_{12}$ aryl, wherein the aryl group is substituted with 1-3 $R^{3a}$ groups each independently $C_1$-$C_6$ alkyl. In some embodiments, $LG^{1b}$ can be $OSO_2R^3$, wherein $R^3$ is Me, $CF_3$ or phenyl, wherein the phenyl is substituted with 1-3 $R^{3a}$ groups each independently hydrogen, $C_1$-$C_6$ alkyl, halogen, or $NO_2$. In some embodiments, $LG^{1b}$ can be $OSO_2R^3$, wherein $R^3$ is Me, $CF_3$ or phenyl, wherein the phenyl is substituted with 1-3 $R^{3a}$ groups each independently hydrogen, Me, F, Cl, Br, or $NO_2$. In some embodiments, $LG^{1b}$ can be $OSO_2R^3$, wherein $R^3$ is phenyl, substituted with 1-3 $R^{3a}$ groups each independently hydrogen, Me, F, Cl, Br, or $NO_2$. In some embodiments, $LG^{1b}$ can be $OSO_2R^3$, wherein $R^3$ is p-tolyl. In some embodiments, $LG^{1b}$ can be I.

In some embodiments, $LG^{1a}$ and $LG^{1b}$ can be $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $LG^{1a}$ and $LG^{1b}$ can be $OSO_2R^3$, wherein $R^3$ is $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $LG^{1a}$ and $LG^{1b}$ can be $OSO_2R^3$, wherein $R^3$ is $C_6$-$C_{12}$ aryl, wherein the aryl group is substituted with 1-3 $R^{3a}$ groups each independently $C_1$-$C_6$ alkyl. In some embodiments, $LG^{1a}$ and $LG^{1b}$ can be $OSO_2R^3$, wherein $R^3$ is Me, $CF_3$ or phenyl, wherein the phenyl is substituted with 1-3 $R^{3a}$ groups each independently hydrogen, $C_1$-$C_6$ alkyl, halogen, or $NO_2$. In some embodiments, $LG^{1a}$ and $LG^{1b}$ can be $OSO_2R^3$, wherein $R^3$ is Me, $CF_3$ or phenyl, wherein the phenyl is substituted with 1-3 $R^{3a}$ groups each independently hydrogen, Me, F, Cl, Br, or $NO_2$. In some embodiments, $LG^{1a}$ and $LG^{1b}$ can be $OSO_2R^3$, wherein $R^3$ is phenyl, substituted with 1-3 $R^{3a}$ groups each independently hydrogen, Me, F, Cl, Br, or $NO_2$. In some embodiments, $LG^{1a}$ and $LG^{1b}$ can be $OSO_2R^3$, wherein $R^3$ is p-tolyl.

Any suitable combination of $R^{1a}$, $R^{1b}$, $LG^{1a}$ and $LG^{1b}$ can be used in the methods disclosed herein. In some embodiments, $R^{1a}$ and $R^{1b}$ can independently be methyl, ethyl, n-propyl, iso-propyl, n-butyl, sec-butyl, iso-butyl, or cyclopropylmethyl, while $LG^{1a}$ and $LG^{1b}$ can independently be Br, I or $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $R^{1a}$ and $R^{1b}$ can independently be methyl, ethyl, n-propyl, iso-propyl, n-butyl, sec-butyl, iso-butyl, or cyclopropylmethyl, while $LG^{1a}$ and $LG^{1b}$ can independently be I or $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, $R^{1a}$ and $R^{1b}$ can be different such that $R^{1a}$ and $R^{1b}$ can independently be methyl, ethyl, n-propyl, iso-propyl, n-butyl, sec-butyl, iso-butyl, or cyclopropylmethyl, while $LG^{1a}$ and $LG^{1b}$ can independently be Br, I or $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $R^{1a}$ can be n-propyl, iso-propyl, n-butyl, sec-butyl, iso-butyl, or cyclopropylmethyl, $R^{1b}$ can be methyl or ethyl, while $LG^{1a}$ can be Br or I, and $LG^{1b}$ can be $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $R^{1a}$ can be iso-propyl, $R^{1b}$ can be methyl, while $LG^{1a}$ can be Br, and $LG^{1b}$ can be $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, $R^{1a}$ can be n-propyl, iso-propyl, n-butyl, sec-butyl, iso-butyl, or cyclopropylmethyl, and $LG^{1a}$ can be Br or I. In some embodiments, $R^{1a}$ can be iso-propyl, and $LG^{1a}$ can be Br. In some embodiments, $R^{1a}$-$LG^{1a}$ can be isopropyl bromide.

In some embodiments, $R^{1b}$ can be methyl or ethyl, and $LG^{1b}$ can be $OSO_2R^3$, wherein $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$. In some embodiments, $R^{1b}$ can be methyl or ethyl, and $LG^{1b}$ can be $OSO_2R^3$, wherein $R^3$ is methyl, trifluoromethyl, 2,2,2-trifluoroethyl, or phenyl, wherein the phenyl is substituted with methyl, bromo or $NO_2$. In some embodiments, $R^{1b}$ can be methyl, and $LG^{1b}$ can be $OSO_2R^3$, wherein $R^3$ is phenyl substituted with methyl. In some embodiments, $LG^{1b}$ can be toluenesulfonyl, p-bromobenzenesulfonyl, nitrobenzenesulfonyl, methanesulfonyl, trifluoromethanesulfonyl, or 2,2,2-trifluoroethyl-1-sulfonyl. In embodiments, $R^{1b}$-$LG^{1b}$ can be methyl tosylate.

In some embodiments, $R^{1a}$ and $R^{1b}$ are the same and can be methyl, ethyl, or cyclopropylmethyl, while $LG^{1a}$ and $LG^{1b}$ can be $OSO_2R^3$, wherein $R^3$ is Me, $CF_3$ or phenyl, wherein the phenyl is substituted with 1-3 $R^{3a}$ groups each independently hydrogen, Me, F, Cl, Br, or $NO_2$. In some embodiments, $R^{1a}$ and $R^{1b}$ can be methyl, ethyl, or cyclopropylmethyl, while $LG^{1a}$ and $LG^{1b}$ can be $OSO_2R^3$, wherein $R^3$ is p-tolyl. In some embodiments, $R^{1a}$ and $R^{1b}$ can be methyl, ethyl, or cyclopropylmethyl, while $LG^{1a}$ and $LG^{1b}$ can be I. In some embodiments, $R^{1a}$ and $R^{1b}$ can be methyl, while $LG^{1a}$ and $LG^{1b}$ can be $OSO_2R^3$, wherein $R^3$ is p-tolyl. In some embodiments, $R^{1a}$ and $R^{1b}$ can be methyl, while $LG^{1a}$ and $LG^{1b}$ can be I. In some embodiments, $R^{1a}$-$LG^{1a}$ and $R^{1b}$-$LG^{1b}$ can be methyl p-toluenesulfonate. In some embodiments, $R^{1a}$-$LG^{1a}$ and $R^{1b}$-$LG^{1b}$ can be methyl iodide.

Any suitable combination of non-nucleophilic base and $R^{1a}$-$LG^{1a}$ of Formula IIIa can be used in the methods disclosed herein. In some embodiments, the non-nucleophilic base can be selected from potassium carbonate, sodium carbonate, potassium tert-butoxide, and sodium tert-butoxide, while $R^{1a}$-$LG^{1a}$ can be selected from isopropyl bromide, methyl p-toluenesulfonate and methyl iodide. In some embodiments, the non-nucleophilic base can be selected from potassium carbonate, and sodium carbonate, while $R^{1a}$-$LG^{1a}$ can be selected from isopropyl bromide, methyl p-toluenesulfonate and methyl iodide. In some embodiments, the non-nucleophilic base can be potassium carbonate, while $R^{1a}$-$LG^{1a}$ can be selected from isopropyl bromide, methyl p-toluenesulfonate and methyl iodide. In some embodiments, the non-nucleophilic base can be potassium carbonate, while $R^{1a}$-$LG^{1a}$ can be methyl p-toluenesulfonate. In some embodiments, the non-nucleophilic base can be potassium carbonate, while $R^{1a}$-$LG^{1a}$ can be methyl iodide. In some embodiments, the non-nucleophilic base can be potassium carbonate, while $R^{1a}$-$LG^{1a}$ can be isopropyl bromide. In some embodiments, the non-nucleophilic base can be selected from potassium tert-butoxide, and sodium tert-butoxide, while $R^{1a}$-$LG^{1a}$ can be selected from methyl p-toluenesulfonate and methyl iodide. In some embodiments, the non-nucleophilic base can be sodium tert-butoxide, while $R^{1a}$-$LG^{1a}$ can be methyl p-toluenesulfonate.

When $R^{1a}$-$LG^{1a}$ and $R^{1b}$-$LG^{1b}$ are the same, any suitable combination of non-nucleophilic base and $R^{1a}$-$LG^{1a}$ and $R^{1b}$-$LG^{1b}$ can be used in the method of the present invention. In some embodiments, the non-nucleophilic base can be selected from potassium carbonate, sodium carbonate, potassium tert-butoxide, and sodium tert-butoxide, while $R^{1a}$-$LG^{1a}$ and $R^{1b}$-$LG^{1b}$ can be selected from isopropyl bromide, methyl p-toluenesulfonate and methyl iodide. In some embodiments, the non-nucleophilic base can be selected from potassium carbonate, and sodium carbonate, while $R^{1a}$-$LG^{1a}$ and $R^{1b}$-$LG^{1b}$ can be selected from isopropyl bromide, methyl p-toluenesulfonate and methyl iodide. In some embodiments, the non-nucleophilic base can be potassium carbonate, while $R^{1a}$-$LG^{1a}$ and $R^{1b}$-$LG^{1b}$ can be selected from isopropyl bromide, methyl p-toluenesulfonate and methyl iodide. In some embodiments, the non-nucleophilic base can be potassium carbonate, while $R^{1a}$-$LG^{1a}$ and $R^{1b}$-$LG^{1b}$ can be methyl p-toluenesulfonate. In some embodiments, the non-nucleophilic base can be potassium carbonate, while $R^{1a}$-$LG^{1a}$ and $R^{1b}$-$LG^{1b}$ can be methyl iodide. In some embodiments, the non-nucleophilic base can be potassium carbonate, while $R^{1a}$-$LG^{1a}$ and $R^{1b}$-$LG^{1b}$ can be isopropyl bromide. In some embodiments, the non-nucleophilic base can be selected from potassium tert-butoxide, and sodium tert-butoxide, while $R^{1a}$-$LG^{1a}$ and $R^{1b}$-$LG^{1b}$ can be selected from methyl p-toluenesulfonate and methyl iodide. In some embodiments, the non-nucleophilic base can be sodium tert-butoxide, while $R^{1a}$-$LG^{1a}$ and $R^{1b}$-$LG^{1b}$ can be methyl p-toluenesulfonate.

A. Two-Step Method

In some embodiments, the methods disclosed herein involve two alkylation steps where the compounds of Formula IIIa and Formula IIIb are different. In some embodiments, the present invention provides a method of making a compound of Formula I:

(I)

substantially free of the compounds of Formula Ia and Formula Ib:

(Ia)

(Ib)

The method of the present invention includes forming a first reaction mixture comprising a compound of Formula II:

(II)

a non-nucleophilic base, a first solvent, and a compound of Formula IIIa:

$R^{1a}$-$LG^{1a}$     (IIIa), wherein the molar ratio of the compound of Formula IIIa to the compound of Formula II is greater than 1, and wherein the reaction mixture is mixed for at least two hours at or above room temperature under conditions suitable to form an intermediate mixture comprising the compound of Formula I and at least one compound of Formula Ia and Ib. The method also includes forming a second reaction mixture comprising the intermediate mixture, and a compound of Formula IIIb:

$R^{1b}$-$LG^{1b}$     (IIIb), wherein the molar ratio of the compound of Formula III to the compounds of the intermediate mixture is greater than 1, and wherein the second reaction mixture is mixed for at least two hours at or above room temperature under conditions suitable to form at least one compound of Formula IVa or Formula IVb:

(IVa)

(IVb)

The method also includes forming a partition mixture comprising the second reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, IIIa, IIIb, IVa and IVb, $R^{1a}$ is methyl, ethyl, n-propyl, iso-propyl, n-butyl, sec-butyl, iso-butyl or cyclopropylmethyl; $R^{1b}$ is methyl, ethyl, n-propyl, iso-propyl, n-butyl, sec-butyl, iso-butyl or cyclopropylmethyl, such that $R^{1b}$ is different than $R^{1a}$; $LG^{1a}$ and $LG^{1b}$ are each independently Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, $R^{1a}$ is ethyl, n-propyl, iso-propyl, n-butyl, sec-butyl, iso-butyl or cyclopropylmethyl; and $R^b$ is methyl.

In some embodiments, the compound of Formula I has the structure:

the compounds of Formula Ia and Formula Ib have the structures:

and the method includes forming the first reaction mixture of the compound of Formula II having the structure:

potassium carbonate, dimethylacetamide, and the compound of Formula IIIa having the structure:

iPr-Br, wherein the molar ratio of the compound of Formula IIIa to the compound of Formula II is greater than 1, and wherein the reaction mixture is mixed for at least two hours at or above room temperature under conditions suitable to form the intermediate mixture comprising the compound of Formula I and at least one compound of Formula Ia or Formula Ib. The method also includes forming the second reaction mixture of the intermediate mixture, dimethylacetamide, and the compound of Formula IIIb:

Me-OTs, wherein the molar ratio of the compound of Formula IIIb to the compounds of the intermediate mixture is greater than 2, and wherein the second reaction mixture is mixed for at least two hours at or above room temperature under conditions suitable to form at least one compound of Formula IVa or Formula IVb:

The method also includes forming the partition mixture of the second reaction mixture, water and dichloromethane to form the aqueous layer and the organic layer, and separating the organic layer and the aqueous layer to isolate the compound of Formula I substantially free of the compounds of Formula Ia, Formula Ib, Formula IVa and Formula IVb.

B. One-Step Method

In some embodiments, the methods disclosed herein involve a single alkylation step where the compounds of Formula IIIa and Formula IIIb are the same. In some embodiments, the present invention provides a method of making a compound of Formula I:

(I)

substantially free of the compounds of Formula Ia and Formula Ib:

(Ia)

(Ib)

The method of the present invention includes forming a first reaction mixture comprising a compound of Formula II:

(II)

the non-nucleophilic base, the first solvent, a compound of Formula IIIa:

$R^{1a}\text{-}LG^{1a}$ (IIIa), and a compound Formula IIIb:

$R^{1b}\text{-}LG^{1b}$ (IIIb), wherein the molar ratio of the compounds of Formula IIIa and IIIb to the compound of Formula II is greater than 2, and wherein the reaction mixture is mixed for at least two hours at or above room temperature under conditions suitable to form the compound of Formula I and at least one compound of Formula IVa or Formula IVb:

(IVa)

(IVb)

The method also includes forming a partition mixture comprising the first reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, IIIa, IIIb, IVa and IVb, $R^{1a}$ and $R^{1b}$ are the same and are methyl, ethyl, n-propyl, iso-propyl, n-butyl, sec-butyl, iso-butyl or cyclopropylmethyl; $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy; $LG^{1b}$ is Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

In some embodiments, the compound of Formula I has the structure:

the compounds of Formula Ia and Formula Ib have the structures:

and the method includes forming the first reaction mixture of the compound of Formula II having the structure:

potassium carbonate, dimethylacetamide, and the compounds of Formula IIIa and IIIb each having the structure:

Me-OTs, wherein the molar ratio of the compounds of Formula IIIa and IIIb to the compound of Formula II is greater than 4, and wherein the reaction mixture is mixed for at least two hours at or above room temperature under conditions suitable to form the compound of Formula I and at least one compound of Formula IVa or Formula IVb having the structures:

The method also includes forming the partition mixture of the first reaction mixture, water and dichloromethane to form the aqueous layer and the organic layer, and separating the organic layer and the aqueous layer to isolate the compound of Formula I substantially free of the compounds of Formula Ia, Formula Ib, Formula IVa and Formula IVb.

In some embodiments where the compounds of Formula IIIa and IIIb are the same, the present invention provides a method of making a compound of Formula I:

substantially free of the compounds of Formula Ia and Formula Ib:

including the step of forming a first reaction mixture of a compound of Formula II:

a non-nucleophilic base, a first solvent, and a compound of Formula III:

$R^1$-LG  (III), wherein the molar ratio of the compound of Formula III to the compound of Formula II is greater than 2, and wherein the reaction mixture is mixed for at least two hours at or above room temperature under conditions suitable to form the compound of Formula I and at least one compound of Formula IVa or Formula IVb:

The methods disclosed herein also include the step of forming a partition mixture including the first reaction mixture, water and an organic solvent to form an aqueous layer and an organic layer, and separating the organic layer and aqueous layer to isolate the compound of Formula I substantially free of the compounds of Formula Ia, Formula Ib, Formula IVa and Formula IVb. For the compounds of Formula I, Ia, Ib, II, III, IVa and IVb, $R^1$ is methyl, ethyl, n-propyl, iso-propyl, n-butyl, sec-butyl, iso-butyl or cyclopropylmethyl, $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy, LG is I or $OSO_2R^3$, and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

The N-alkylation step of forming the compound of Formula I can be performed using any suitable molar ratio of the compound of Formula III to the compound of Formula II. Representative molar ratios include, but are not limited to, greater than 2, or 3, 4, 5, 6, 7, 8, 9 or greater than 10. The molar ratio of the compound of Formula III to the compound of Formula II can be from greater than 2 to about 10, or from greater than 2 to about 5, or from about 3 to about 5. In some embodiments, the molar ratio of the compound of Formula III to the compound of Formula II can be greater than two. In some embodiments, the molar ratio of the compound of Formula III to the compound of Formula II can be from greater than 2 to about 4. In some embodiments, the molar ratio of the compound of Formula III to the compound of Formula II can be about four.

Any suitable combination of non-nucleophilic base and $R^1$-LG of Formula III can be used in the methods disclosed herein. In some embodiments, the non-nucleophilic base can be selected from potassium carbonate, sodium carbonate, potassium tert-butoxide, and sodium tert-butoxide, while $R^1$-LG can be selected from methyl p-toluenesulfonate and methyl iodide. In some embodiments, the non-nucleophilic base can be selected from potassium carbonate, and sodium carbonate, while $R^1$-LG can be selected from methyl p-toluenesulfonate and methyl iodide. In some embodiments, the non-nucleophilic base can be potassium carbonate, while $R^1$-LG can be selected from methyl p-toluenesulfonate and methyl iodide. In some embodiments, the non-nucleophilic base can be potassium carbonate, while $R^1$-LG can be methyl p-toluenesulfonate. In some embodiments, the non-nucleophilic base can be potassium carbonate, while $R^1$-LG can be methyl iodide. In some embodiments, the non-nucleophilic base can be selected from potassium tert-butoxide, and sodium tert-butoxide, while $R^1$-LG can be selected from methyl p-toluenesulfonate and methyl iodide. In some embodiments, the non-nucleophilic base can be sodium tert-butoxide, while $R^1$-LG can be methyl p-toluenesulfonate.

In some embodiments where the compounds of Formula IIIa and IIIb are the same, the methods disclosed herein provide a method of preparing the compound of Formula I having the structure:

substantially free of the compounds of Formula Ia and Formula Ib having the structures:

including the step of forming the first reaction mixture of the compound of Formula II having the structure:

potassium carbonate, dimethylacetamide, and the compounds of Formula IIIa and Formula IIIb having the structure:

Me-OTs, wherein the molar ratio of the compounds of Formula IIIa and IIIb to the compound of Formula II is greater than 4, and wherein the reaction mixture is mixed for at least two hours at or above room temperature under conditions suitable to form the compound of Formula I and at least one compound of Formula IVa or Formula IVb having the structures:

forming the partition mixture including the first reaction mixture, water and dichloromethane to form the aqueous layer and the organic layer; and separating the organic layer and the aqueous layer to isolate the compound of Formula I substantially free of the compounds of the compounds of Formula Ia, Formula Ib, Formula IVa and Formula IVb.

In some embodiments, the methods disclosed herein provide a method of preparing a compound of Formula I having the structure:

substantially free of the compounds of Formula Ia and Formula Ib having the structures:

including the step of forming the first reaction mixture of the compound of Formula II having the structure:

potassium carbonate, dimethylacetamide, and the compound of Formula III having the structure:

Me-OTs, wherein the molar ratio of the compound of Formula III to the compound of Formula II is about 4, and wherein the reaction mixture is mixed for at least two hours at or above room temperature under conditions suitable to form the compound having the structure:

and at least one compound of Formula IVa or Formula IVb having the structures:

forming the partition mixture including the first reaction mixture, water and dichloromethane to form the aqueous layer and the organic layer; and separating the organic layer and the aqueous layer to isolate the compound having the structure:

substantially free of the compounds having the structures:

IV. Method of Preparing Triazoles of the Formula II

In some embodiments, the methods disclosed herein provide a method of preparing a compound of Formula II:

(II)

wherein $R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy.

In some embodiments, the present invention provides a method of preparing a compound having the structure:

including the step of forming a first reaction mixture of sodium 2H-1,2,3-triazole-4-thiolate, ethanol, and benzyl bromide, under conditions suitable to form the benzyl thio compound.

V. EXAMPLES

Example 1. One-Step Alkylation Method for Preparation of 4-(benzylthio)-2-methyl-2H-1,2,3-triazole Preparation of 4-(benzylthio)-2-methyl-2H-1,2,3-triazole is described.

Preparation of 4-(benzylthio)-2H-1,2,3-triazole

Benzyl bromide (11.79 mL, 99 mmol) was added dropwise to a solution of sodium 2H-1,2,3-triazole-4-thiolate (12.2 g, 99 mmol) in ethanol (100 mL) at 0° C. The reaction mixture was allowed to warm to room temperature and stirred for 20 minutes. The reaction mixture was diluted with ethyl acetate (100 mL) and washed with water (100 mL), brine (100 mL) and then dried (sodium sulfate). The solvent was removed to give 4-(benzylthio)-2H-1,2,3-triazole (16.9 g) as a white solid, LCMS: RT 1.66 min, m+H=191; $^1$H NMR (400 MHz, CDCl$_3$): δ 9.72 (1H, v br s), 7.47 (1H, s), 7.30-7.21 (5H, m), 4.12 (2H, s).

Alternative Preparation of 4-(Benzylthio)-2H-1,2,3-Triazole

Sodium 1H-1,2,3-triazole-4-thiolate.

(250.0 g, 1929 mmol, 1 equivalent) was suspended in 1250 mL of ethanol. Benzyl bromide (320 g, 224 mL, 1871 mmol, 0.97 equivalents) was added drop wise over a period of 1 hour at 20° C. The dosing bulb was rinsed with 250 mL of ethanol. The resulting suspension was stirred for 1 hour. Analyses indicated full consumption of the benzyl bromide. The reaction mixture was concentrated to 500 mL by distilling under reduced pressure. Next, 500 mL MTBE, 500 mL 20% sodium chloride solution and 250 mL of water were added and the mixture was stirred until a clear solution was obtained. The layers were separated and the aqueous layer was extracted one time with 250 mL of MTBE. The organic layers were combined and the mixture was partially concentrated to approximately 700 mL by distilling at reflux under atmospheric pressure. Weight of solution 705 g, 52 wt % of 4-(benzylthio)-2H-1,2,3-triazole, (358 g, 1871 mmol, 97%). The crude solution was used directly in the next step without the need for purification.

Preparation of
4-(benzylthio)-2-methyl-2H-1,2,3-triazole

Potassium carbonate (188 g, 1358 mmol, 2 equivalents) and 4-(benzylthio)-2H-1,2,3-triazole (130 g, 680 mmol, 1 equivalent) in approximately 50 mL of MTBE/ethanol mixture were suspended in 700 mL of dimethylacetamide. Methyl p-toluenesulfonate (506 g, 2710 mmol, 4 equivalents) was added dropwise over a period of 45 min. Afterwards the dosing bulb was rinsed with 100 mL of dimethylacetamide. The resulting reaction mixture was heated to 40° C. and stirred for 65 hours. Analyses indicated that the ratio between the desired regioisomer and the alternative regioisomers was >95:5 area %. The resulting mixture was heated to 60° C. and stirred for 24 hours. The ratio was further increased to 96.9:3.1 area % and the amount of methyl p-toluenesulfonate had decreased to <2.0 area %. The mixture was cooled to 20° C. and 1040 mL of water was added dropwise. The mixture was stirred until a clear solution was obtained. Next, 500 mL of dichloromethane (4 rel. volumes) was added and the layers were separated. The aqueous layer was extracted two more times with 250 mL of dichloromethane. The organic layers were combined and washed two times with 500 mL of water. The mixture was concentrated to 265 mL by distilling at reflux under atmospheric pressure. Weight of solution 364 g, 16.2 wt % of 4-(benzylthio)-2-methyl-2H-1,2,3-triazole (59.0, 286 mmol, 42%). The crude solution can be used directly in a subsequent step without the need for purification.

Example 2: Two-Step Alkylation Method for Preparation of 4-(benzylthio)-2-isopropyl-2H-1,2,3,triazole A crude solution of 4-(benzylthio)-2H-1,2,3-triazole (as prepared in Example 1) and potassium carbonate (2 equivalents) in dimethylacetamide was heated to 40° C. and then 2-bromopropane (1.5 equivalents) was added over 6 minutes. The resultant mixture was stirred for 22 hours (ratio desired regioisomer to undesired isomers 67:13:20) and then methyl p-toluenesulfonate (2.5 equivalents) in dimethylacetamide was added over 6 minutes. The resultant mixture was stirred at 40° C. for 2 days (ratio desired regioisomer to undesired isomers 96.8:2.4:0.8) and then heated to 60° C. to destroy any excess methyl p-toluenesulfonate. After stirring at 60° C. for 23 hours the reaction mixture was quenched by the addition of water and the mixture was extracted 3 times with dichloromethane. The organic phases were combined and washed several times with water and then concentrated at atmospheric pressure. The resultant solution was used directly in the next step of the synthesis without the need for purification.

Although the foregoing invention has been described in some detail by way of illustration and example for purposes of clarity of understanding, one of skill in the art will appreciate that certain changes and modifications may be practiced within the scope of the appended claims. In addition, each patent, patent application, patent publication, and reference provided herein is incorporated by reference in its entirety to the same extent as if each reference was individually incorporated by reference. Where a conflict exists between the instant application and a reference provided herein, the instant application shall dominate.

What is claimed is:

1. A method of making a compound of Formula I:

(I)

substantially free of the compounds of Formula Ia and Formula Ib:

(Ia)

(Ib)

comprising:
a) forming a first reaction mixture comprising a compound of Formula II:

(II)

a non-nucleophilic base, a first solvent, and a compound of Formula IIIa:

$R^{1a}$-$LG^{1a}$ (IIIa), wherein the molar ratio of the compound of Formula IIIa to the compound of Formula II is greater than 1, under conditions suitable to form an intermediate mixture comprising the compound of Formula I and at least one compound of Formula Ia and Ib;

a1) forming a second reaction mixture comprising the intermediate mixture, and a compound of Formula IIIb:

$R^{1b}$-$LG^{1b}$ (IIIb)

wherein the molar ratio of the compound of Formula IIIb to the compounds of the intermediate mixture is greater than 1, and wherein the second reaction mixture is mixed under conditions suitable to form at least one compound of Formula IVa or Formula IVb:

(IVa)

(IVb)

b) forming a partition mixture comprising the second reaction mixture, water and an organic solvent to form an aqueous layer and an organic layer; and
c) separating the organic layer and aqueous layer to isolate the compound of Formula I substantially free of the compounds of Formula Ia, Formula Ib, Formula IVa and Formula IVb, wherein

$R^{1a}$ and $R^{1b}$ are independently methyl, ethyl, n-propyl, iso-propyl, n-butyl, sec-butyl, iso-butyl or cyclopropylmethyl;

$R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$haloalkyl, $C_1$-$C_6$ alkoxy, or $C_1$-$C_6$ haloalkoxy;

$LG^{1a}$ and $LG^{1b}$ are each independently Br, I or $OSO_2R^3$; and $R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

2. The method of claim 1, wherein the compounds of Formula IIIa and IIIb are different, such that the method comprises
a) forming the first reaction mixture comprising a compound of Formula II:

(II)

the non-nucleophilic base, the first solvent, and the compound of Formula IIIa:

$R^{1a}$-$LG^{1a}$ (IIIa), wherein the molar ratio of the compound of Formula IIIa to the compound of Formula II is greater than 1, and wherein the reaction mixture is mixed for at least two hours at or above room temperature under conditions suitable to form the intermediate mixture comprising the compound of Formula I and at least one compound of Formula Ia and Ib;

a1) forming the second reaction mixture comprising the intermediate mixture, and the compound of Formula IIIb:

$R^{1b}$-$LG^{1b}$ (IIIb)

wherein the molar ratio of the compound of Formula III to the compounds of the intermediate mixture is greater than 1, and wherein the second reaction mixture is mixed for at least two hours at or above room temperature under conditions suitable to form at least one compound of Formula IVa or Formula IVb:

(IVa)

(IVb)

b) forming the partition mixture comprising the second reaction mixture, water and the organic solvent to form the aqueous layer and the organic layer; and c) separating the organic layer and aqueous layer to isolate the compound of Formula I substantially free of the compounds of Formula Ia, Formula Ib, Formula IVa and Formula IVb, wherein
$R^{1a}$ is methyl, ethyl, n-propyl, iso-propyl, n-butyl, sec-butyl, iso-butyl or cyclopropylmethyl;
$R^{1b}$ is methyl, ethyl, n-propyl, iso-propyl, n-butyl, sec-butyl, iso-butyl or cyclopropylmethyl, such that $R^{1b}$ is different than $R^{1a}$;
$LG^{1a}$ and $LG^{1b}$ are each independently Br, I or $OSO_2R^3$; and
$R^3$ is $C_1$-$C_6$ alkyl, $C_1$-$C_6$ haloalkyl, or $C_6$-$C_{12}$ aryl, wherein the aryl group is substituted with 1-3 $R^{1a}$ groups each independently hydrogen, $C_1$-$C_6$ alkyl, halogen, or $NO_2$.

3. The method of claim 1, wherein
$R^{1a}$ is ethyl, n-propyl, iso-propyl, n-butyl, sec-butyl, iso-butyl or cyclopropylmethyl; and
$R^{1b}$ is methyl.

4. The method of claim 1, wherein the compounds of Formula IIIa and IIIb are the same, such that the method comprises:

a) forming the first reaction mixture comprising the compound of Formula II, the non-nucleophilic base, the first solvent, and the compounds of Formula IIIa and IIIb, wherein the molar ratio of the compounds of Formula IIIa and IIIb to the compound of Formula II is greater than 2, and wherein the reaction mixture is mixed for at least two hours at or above room temperature under conditions suitable to form the compound of Formula I and at least one compound of Formula IVa or Formula IVb:

(IVb)

b) forming the partition mixture comprising the first reaction mixture, water and the organic solvent to form the aqueous layer and the organic layer; and c) separating the organic layer and aqueous layer to isolate the compound of Formula I substantially free of the compounds of Formula Ia, Formula Ib, Formula IVa and Formula IVb, wherein
$R^{1a}$ and $R^{1b}$ are the same and are methyl, ethyl, n-propyl, iso-propyl, n-butyl, sec-butyl, iso-butyl or cyclopropylmethyl;
$R^2$ is halogen, $SCH_2Ar$ or $SCHAr_2$, wherein each Ar is phenyl optionally substituted with 1-3 $R^{2a}$ groups each independently halogen, $C_1$-$C_6$ alkyl, $C_1$-$C_6$ haloalkyl, $C_1$-$C_6$ alkoxy, or $C_1$-$C_6$ haloalkoxy;
$LG^{1b}$ is Br, I or $OSO_2R^3$; and
$R^3$ is $C_1$-$C_6$ alkyl, $C_1$-$C_6$ haloalkyl, or $C_6$-$C_{12}$ aryl, wherein the aryl group is substituted with 1-3 $R^{3a}$ groups each independently hydrogen, $C_1$-$C_6$ alkyl, halogen, or $NO_2$.

5. The method of claim 1, wherein the compounds of Formula IIIa and IIIb are the same, such that the method comprises:

a) forming the first reaction mixture comprising the compound of Formula II, the non-nucleophilic base, the first solvent, and the compounds of Formula IIIa and IIIb, wherein the molar ratio of the compounds of Formula IIIa and IIIb to the compound of Formula II is greater than 2, and wherein the reaction mixture is mixed for at least two hours at or above room temperature under conditions suitable to form the compound of Formula I and at least one compound of Formula IVa or Formula IVb:

(IVa)

(IVb)

b) forming the partition mixture comprising the first reaction mixture, water and the organic solvent to form the aqueous layer and the organic layer; and c) separating the organic layer and aqueous layer to isolate the compound of Formula I substantially free of the compounds of Formula Ia, Formula Ib, Formula IVa and Formula IVb, wherein R$^{1a}$ and R$^{1b}$ are the same and are methyl, ethyl, n-propyl, iso-propyl, n-butyl, sec-butyl, iso-butyl or cyclopropylmethyl;

R$^2$ is halogen, SCH$_2$Ar or SCHAr$_2$, wherein each Ar is phenyl optionally substituted with 1-3 R$^{2a}$ groups each independently halogen, C$_1$-C$_6$ alkyl, C$_1$-C$_6$ haloalkyl, C$_1$-C$_6$ alkoxy, or C$_1$-C$_6$ haloalkoxy;

LG$^{1b}$ is I or OSO$_2$R$^3$; and

R$^3$ is C$_1$-C$_6$ alkyl, C$_1$-C$_6$ haloalkyl, or C$_6$-C$_{12}$ aryl, wherein the aryl group is substituted with 1-3 R$^{1a}$ groups each independently hydrogen, C$_1$-C$_6$ alkyl, halogen, or NO$_2$.

6. The method of claim 1, wherein the non-nucleophilic base is selected from the group consisting of potassium carbonate, sodium carbonate, potassium tert-butoxide, and sodium tert-butoxide.

7. The method of claim 1, wherein the non-nucleophilic base is potassium carbonate.

8. The method of claim 1, wherein the first solvent is selected from the group consisting of acetone, acetonitrile, dimethylacetamide, tetrahydrofuran, dimethylsulfoxide, toluene, methyl tert-butyl ether, ethanol, and dimethylformamide, or combinations thereof.

9. The method of claim 1, wherein the first solvent is selected from the group consisting of dimethylacetamide, methyl tert-butyl ether, and ethanol, or combinations thereof.

10. The method of claim 1, wherein the first solvent is dimethylacetamide.

11. The method of claim 1, wherein the first reaction mixture is maintained at a temperature of from about room temperature to about 40° C.

12. The method of claim 1, wherein the first reaction mixture is mixed for at least eight hours.

13. The method of claim 1, wherein the organic solvent in the partition mixture is dichloromethane.

14. The method of claim 4, wherein R$^{1a}$ and R$^{1b}$ are methyl.

15. The method of claim 1, wherein R$^2$ is SCH$_2$Ar, wherein Ar is phenyl.

16. The method of claim 1, wherein R$^2$ is halogen.

17. The method of claim 1, wherein

LG$^{1b}$ is OSO$_2$R$^3$; and

R$^3$ is C$_1$-C$_6$ alkyl, C$_1$-C$_6$ haloalkyl, or C$_6$-C$_{12}$ aryl, wherein the aryl group is substituted with 1-3 R$^{1a}$ groups each independently hydrogen, C$_1$-C$_6$ alkyl, halogen, or NO$_2$.

18. The method of claim 1, wherein

LG$^{1b}$ is OSO$_2$R$^3$; and

R$^3$ is C$_6$-C$_{12}$ aryl substituted with 1-3 R$^{1a}$ groups each independently hydrogen, C$_1$-C$_6$ alkyl, halogen, or NO$_2$.

19. The method of claim 1, wherein

LG$^{1b}$ is OSO$_2$R$^3$; and

R$^3$ is C$_6$-C$_{12}$ aryl substituted with 1-3 R$^{1a}$ groups each independently C$_1$-C$_6$ alkyl.

20. The method of claim 1, wherein

LG$^{1b}$ is OSO$_2$R$^3$; and

R$^3$ is p-tolyl.

21. The method of claim 1, wherein LG$^{1b}$ is I.

22. The method of claim 1, wherein the compound of Formula I has the structure:

the compounds of Formula Ia and Formula Ib have the structures:

and the method comprises:

a) forming the first reaction mixture comprising the compound of Formula II having the structure:

potassium carbonate, dimethylacetamide, and the compounds of Formula IIIa and IIIb each having the structure:

Me-OTs, wherein the molar ratio of the compounds of Formula IIIa and IIIb to the compound of Formula II is greater than 4, and wherein the reaction mixture is mixed for at least two hours at or above room temperature under conditions suitable to form the compound of Formula I and at least one compound of Formula IVa or Formula IVb having the structures:

b) forming the partition mixture comprising the first reaction mixture, water and dichloromethane to form the aqueous layer and the organic layer; and c) separating the organic layer and the aqueous layer to isolate the compound of Formula I substantially free of the compounds of Formula Ia, Formula Ib, Formula IVa and Formula IVb.

23. The method of claim 1, wherein the compound of Formula I has the structure:

the compounds of Formula Ia and Formula Ib have the structures:

and the method comprises:
a) forming the first reaction mixture comprising the compound of Formula II having the structure:

potassium carbonate, dimethylacetamide, and the compound of Formula IIIa having the structure:

iPr-Br, wherein the molar ratio of the compound of Formula IIIa to the compound of Formula II is at least 1, and wherein the reaction mixture is mixed for at least two hours at or above room temperature under conditions suitable to form the intermediate mixture comprising the compound of Formula I and at least one compound of Formula Ia or Formula Ib;

a1) forming the second reaction mixture comprising the intermediate mixture, dimethylacetamide, and the compound of Formula IIIb:

Me-OTs, wherein the molar ratio of the compound of Formula IIIb to the compounds of the intermediate mixture is greater than 2, and wherein the second reaction mixture is mixed for at least two hours at or above room temperature under conditions suitable to form at least one compound of Formula IVa or Formula IVb:

b) forming the partition mixture comprising the second reaction mixture, water and dichloromethane to form the aqueous layer and the organic layer; and c) separating the organic layer and the aqueous layer to isolate the compound of Formula I substantially free of the compounds of Formula Ia, Formula Ib, Formula IVa and Formula IVb.

* * * * *

UNITED STATES PATENT AND TRADEMARK OFFICE
CERTIFICATE OF CORRECTION

PATENT NO. : 10,494,349 B2  
APPLICATION NO. : 16/390169  
DATED : December 3, 2019  
INVENTOR(S) : Hazel Hunt, Arjen Christiaan Breman and Bas Wilhelmus Theodorus Gruijters Page 1 of 1

It is certified that error appears in the above-identified patent and that said Letters Patent is hereby corrected as shown below:

In the Claims

In Column 31, Line 39, delete "1-3 $R^{1a}$" and replace with --1-3 $R^{3a}$--

In Column 33, Line 12, delete "1-3 $R^{1a}$" and replace with --1-3 $R^{3a}$--

In Column 33, Line 50, delete "1-3 $R^{1a}$" and replace with --1-3 $R^{3a}$--

In Column 33, Line 56, delete "1-3 $R^{1a}$" and replace with --1-3 $R^{3a}$--

In Column 33, Line 61, delete "1-3 $R^{1a}$" and replace with --1-3 $R^{3a}$--

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*